United States Patent
Schwarz

(10) Patent No.: US 6,251,402 B1
(45) Date of Patent: *Jun. 26, 2001

(54) USE OF HUMAN CHORIONIC GONADOTROPIN IN THE TREATMENT OF KAPOSI'S SARCOMA

(75) Inventor: Siegfried Schwarz, Innsbruck (AT)

(73) Assignee: Applied Research Systems ARS Holding N.V., Curacao (AN)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/101,640

(22) PCT Filed: Oct. 11, 1996

(86) PCT No.: PCT/EP96/04415

§ 371 Date: Apr. 29, 1999

§ 102(e) Date: Apr. 29, 1999

(87) PCT Pub. No.: WO97/14428

PCT Pub. Date: Apr. 24, 1997

(30) Foreign Application Priority Data

Oct. 16, 1995 (IT) .............................................. RM95A0686
May 7, 1996 (IT) .............................................. RM96A0309

(51) Int. Cl.⁷ .............................. A61K 39/00; C07K 14/59

(52) U.S. Cl. ........................................ 424/198.1; 530/398

(58) Field of Search ........................... 530/398; 424/198.1

(56) References Cited

U.S. PATENT DOCUMENTS 5,677,275   10/1997   Lunardi-Iskandar et al. .

OTHER PUBLICATIONS

Sairam, M.R., "Hormonal Antagonistic Properties of Deglycosylated Pituitary Lutropin" in "Horm. Act. Brain Pept.: Struct. Funct", McKerns et al., Ed., Plenum Press, NY, pp. 85–97, 1983.*

Birken et al., "Structure of the Human Chorionic Gonadotropin β–Subunit Fragment from Pregnancy Urine", Endocrinology, 123(1), pp. 572–583, Jul. 1988.*

Kalyan et al., "Role of Carbohydrate in Human Chorionic Gonadotropin", J. Biol. Chem., 258(1), pp. 67–74, Jan. 1983.*

Lunardi–Iskandar et al., Tumorigenesis and Metastasis of Neoplastic Kaposi's Sarcoma Cell Line in Immunodeficient Mice Blocked by a Human Pregnancy Hormone, Nature, vol. 375, pp. 64–68, May 1995.*

Schwarz et al., "Visualization of Differences in Receptor Iteraction Between Native, Deglycosylated and Asialo Human Chorionic Gonadotropin (hCG) by Monoclonal Antibodies", ACTA Endocrinologica, vol. 122, Suppl. 1, p. 42, Mar. 1990.*

Samaniego et al., "β–Human Chorionic Gonadotropin (βHCG) Induces Programmed Cell Death in AIDS–Associated Kaposi's Sarcoma (AIDS–KS) Cells", AIDS Res. Hum. Retrovir., vol. 10, Suppl. 3, p. S102, Abstr. 158, Sep. 1994.*

Sigma Catalog, pp. 264–265, 1994.*

* cited by examiner

Primary Examiner—Jon P. Weber
(74) Attorney, Agent, or Firm—Browdy and Neimark

(57) ABSTRACT

The use of hCG Beta-core or hCG fragments, deglycosylated hCG in the treatment of Kaposi's sarcoma is described. Inhibition of tumor production or regression on a variety of KS cell lines is shown. Purified hCG preparations do not inhibit the growth of KS cell lines.

5 Claims, 1 Drawing Sheet

SEQUENCE LISTING

```
<160> NUMBER OF SEQ ID NOS: 4

<210> SEQ ID NO: 1
<211> LENGTH: 27
<212> TYPE: DNA
<213> ORGANISM: Human

<400> SEQUENCE: 1
cctggaggcc acgttgactt accccag                               27

<210> SEQ ID NO: 2
<211> LENGTH: 25
<212> TYPE: DNA
<213> ORGANISM: Human

<400> SEQUENCE: 2
cctaaggaag tcatagccca taatg                                 25

<210> SEQ ID NO: 3
<211> LENGTH: 22
<212> TYPE: DNA
<213> ORGANISM: Human
```

-continued

```
<400> SEQUENCE: 3
atgcctgccg tgtgaaccat gt                                    22

<210> SEQ ID NO: 4
<211> LENGTH: 22
<212> TYPE: DNA
<213> ORGANISM: Human

<400> SEQUENCE: 4
agagctacct gtggagcaac ct                                    22
```

USE OF HUMAN CHORIONIC GONADOTROPIN IN THE TREATMENT OF KAPOSI'S SARCOMA

CROSS-REFERENCE TO RELATED APPLICATION

The present application is a national phase application under 35 U.S.C. §371 of PCT/EP96/04415, filed Oct. 11, 1996.

FIELD OF THE INVENTION

The present invention relates to the use of hCG fragments or deglycosylated hCG in the treatment of Kaposi's sarcoma. In particular the invention relates to the use of hCG Beta-core in the treatment of Kaposi's sarcoma.

BACKGROUND ART

Kaposi's sarcoma (KS) is a neoplastic disease characterised by highly vascularized lesions, closely related with epidemic HIV and which occasionally occurs in patients who underwent transplantation, as a consequence of the immunosuppression. KS occurs more often in men than in women and HIV-associated KS has a high occurrence in homosexual men. Most cultures of KS tumours yield cells with properties of hyperplastic (not malignant) endothelial cells under the control of several cytokines.

hCG is a hormone secreted by the placenta as well as by a number of various other tissues, normal and neoplastic ones. It is secreted and acts so in both an endocrine and paracrine way. hCG is heterodimer consisting of an α-subunit and a β-subunit.

Surprisingly, each of them shares a structural feature, the so called cystine-knot motif, with several growth factors (NGF, PDGF and others) that are otherwise unrelated to HCG or to the family of glycoprotein hormones, as it has been recently elucidated by crystal structure analysis of deglycosylated HCG. Until now, there is only one receptor known that binds with high affinity ($\approx 0.01$ $\mu$M) hCG, but also luteinising hormone (LH), that is almost identical to hCG, except for a C terminal extension in hCG.

This receptor, referred to as the LH/hCG-R, as well as those of the other glycoprotein hormones, has been recently cloned and results to belong to the superfamily of 7-transmembrane helix/G protein-coupled receptors, from which it is however distinct due to the long extracellular domain, acting as the ligand capturing element. Such kind of receptors is encoded by a mosaic gene, consisting of 10 exons, representing 11 of the so called leucine rich repeats (LRM), and a 11th exon, representing 3 LRM's and the entire transmembrane module. The ensemble of the 14 LRM's is currently thought to form a horse-shoe structure "embracing" the ligand. The receptor of glycoprotein hormones binds only the respective entire hormone, but not a single subunit. The circulating hormone is in the subnanomolar range, as are the affinity for the respective receptor. Only during early pregnancy, the blood levels of hCG rise up to suprananomolar levels, and a fraction (about $\approx 0.001$) occurs also as free subunit.

Besides dissociated subunits, a variety of other metabolic forms of hCG, particularly in urine, can be found, such as glycosylation and sialylation variants (isoforms), nicked hCG and a particular fragment of β subunit called "Beta-core". Such fragment has been purified by affinity extraction by using monoclonal antibodies (Birken et al., Endocrinology, 123: 572–583, 1988). The amino acid sequence of the fragment has been determined. Beta-core consists of two polypeptides, bound by disulphide bridges, which correspond to residues 6–40 and 55–92 of hCG β-subunit.

In addition to the above mentioned isoforms, deglycosylated hCG can be obtained by different chemical and/or biotechnological ways as described, for example, by Kalyan e Bahl, J. Biol. Chem. 258: 67–74, 1983.

Beta-core, as deglycosylated hCG or the single isolated subunits, does not show hCG-like biological activity, but represents a major form of immunoreactive hCG and can contaminate pharmaceutical preparation of urinary hCG.

Lunardi-Iskandar et al., Nature, 375: 64–68, 1995 have shown that hCG and the hCG β-subunit inhibit the growth of KS cell lines derived from Kaposi's sarcoma, and inhibit tumour production by such cell lines in nude mice. Regression of Kaposi's sarcoma has been shown in two women during pregnancy, when the level of such hormone is high.

DISCLOSURE OF THE INVENTION

Figure 1:
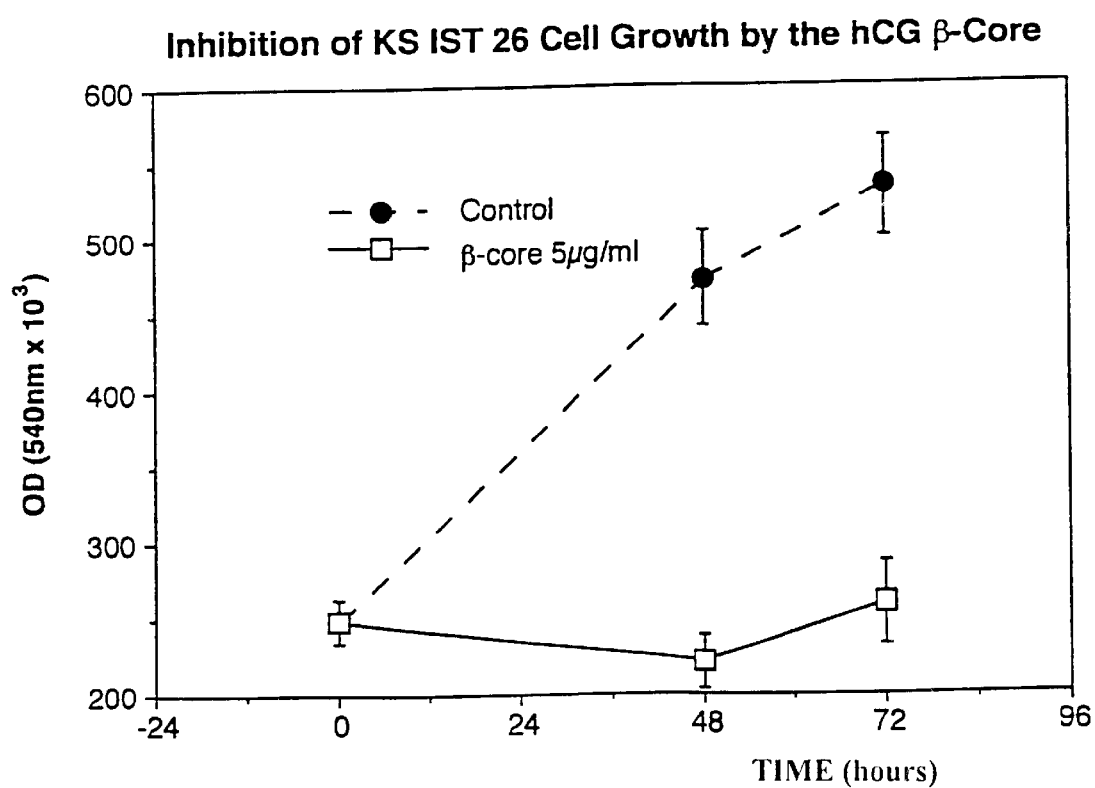
FIG. 1 is a graph showing the effect of hCG β-core on the growth of Kaposi's sarcoma spindle cells and on cultured normal human umbilical vein endothelial cells (control).

We have now found that membranes of KS cells as defined above do not contain the specific hCG/hLH receptor, whereas they contain binding sites of Beta-core and deglycosylated hCG and we hypothesise that impurities contained in hCG preparations, hCG fragments or degradation products, such as Beta-core itself and/or deglycosylated hCG and/or fragments which do not bind the hCG receptor and do not exert hCG-like biological activity are responsible for the in vivo and in vitro activities found by Lunardi-Iskandar. Other fragments or degradation products of hCG comprising all or part of the Beta-core region can be responsible for this activity as well. Impure luteinising hormone (LH), its β-subunit and Beta-core can be also used for killing or inhibit KS cell lines, due to the almost identity of LH and hCG sequences, as reported above. Other tumoral forms can be equally treated with Beta-core or with deglycosylated hCG/LH. Object of the present invention is, therefore, the use of hCG fragments of degradation products which do not bind the hCG receptor and do not exert hCG-like biological activity for the preparation of a medicament for the treatment of Kaposi's sarcoma or other tumoral forms. In particular, the hCG fragments are hCG Beta-core, hCG fragments containing all or part of the Beta-core sequence, deglycosylated hCG or deglycosylated LH.

In the course of our study on the effect of hCG and its derivatives on KS cells, it has been observed that hCG does not bind to KS membranes, whereas a low affinity binding at nanomolar concentration has been evidenced when using deglycosylated hCG and hCG Beta-core.

We have further analysed four different specimens of KS, obtained by informed consent of four different HIV patients, in order to verify the presence of LH/hCG receptor. The specimens have been histopathologically verified. By using saturation analysis with $^{125}$I-hCG, a specific binding has not been detected in any of such KS samples, although the total membrane protein was the same as in of rat testis membranes used as positive control for LH/hCG-R.

We have also analysed four different epidemic KS cell lines for evidencing mRNA expression of LH/hCG receptor using reverse transcription PCR. By using a pair of primers for the ninth and eleventh exon, mRNA expression of LH/hCG-R has not been evidenced in any of the four KS cell lines, whereas human testis resulted clearly positive.

We thus come to the conclusion that the growth inhibition of KS Y-1 cell line (Lunardi-Iskandar et al.) in the pregnant nude mice or in nude mice treated with hCG is mediated by a mechanism distinct from the classical interaction with the LH/hCG-R or by non-LH-hCG substance, which were possibly present in the preparations or in the in vivo settings used in those experiments.

A recombinant Beta-core molecule can also be engineered in order to evaluate its potential biological activity. The Beta-core fragment has, among other things, a loop deletion (the "Keutmann loop") at position Thr40 and Val 55. This loop can be replaced by a smaller one with a high probability to energetically favour a Beta-turn loop formation. The distance between the Cα of Thr40 and Val55 is 7.2 Å. A linker such as ProGlyAla was chosen and appeared to fit well the gap between these residues. The ProGlyAla linker easily favours a turn formation.

Another characteristic of the Beta-core fragment is the presence of a free and accessible cysteine at position 21. A recombinant Beta-core molecule containing a free cysteine might tend to make a disulfide homodimer molecule. A free cysteine might also represent an opportunity to specifically modify the molecule by coupling to biodegradable polymer such as PEG. As it is still unclear whether the potential biological activity of the Beta-core fragment is related to its monomeric or dimeric form, the native recombinant Beta-core molecule and its mutant Cys21-Ala rBeta-core molecule are best expressed in CHO cells.

EXAMPLE 1

Binding to Kaposi's Sarcoma membranes

Membranes extracted from biopsies of KS were incubated in increasing concentration, from $1\times10^{-6}$ to $1\times10\times^{-10}$ M, of $^{125}$I-hCG or HCG β subunit, deglycosylated hCG, hCG Beta-core, followed by incubation with an $^{125}$I-labelled antibody to hCG Beta-core. The same substances have been tested on rat testis membranes, as control. It was observed that KS membranes did not bind hCG, whereas such binding occurred at high affinity on rat testis membranes. Deglycosylated hCG and hCG Beta-core showed a low affinity binding at nanomolar concentration with both KS and rat testis membranes.

mRNA Isolation

In order to verify whether mRNA expression of LH/hCG receptor occurs, reverse transcription PCR was used starting from mRNA isolated from four different epidemic KS cell lines, named M7/3, M5/1, M7/KK2 and KS10 (Table 1).

From all samples mRNA was extracted using a solid phase affinity chromatography on poly-T resin, according to the manufacturer's instructions (R&D Systems Europe Ltd. "mini message make" RNA Isolation Kit). The cells were harvested, washed twice with 25 ml of phosphate buffer (PBS) at room temperature (1000 rpm, 5 min, Beckman TJ6) and the pellets were frozen in liquid nitrogen. The pellets were then solubilized with 1 ml of "lysis buffer" (if necessary, several harvests were pooled), and 50 µl oligo-dT latex beads were added, and incubated at room temperature for 10 minutes. Beads were spun down (12000 rpm, 5 min), transferred to a "spin column", that was washed twice with "wash buffer" (12000 rpm, 30 sec and 2 min, respectively), and finally eluted with 50 µl 70° C. "elution buffer". RNA yield was estimated by $OD_{260}/OD_{280}$ nm method. Eluates were stored at −80° C.

cDNA preparation

Aliquots of 200–500 ng mRNA were reverse transcribed using the following procedure: 1–10 µl mRNA eluate were mixed with 1 µl oligo-dT-15 solution (500 ng/ml, PROMEGA), incubated 10 min at 70° C., cooled on ice, centrifuged (12000 rpm, 6 sec). Thereafter, 4 µl 5× "1st strand buffer" (PROMEGA kit), 2 µl 0.1 M DTT, 1 µl dNTP's (10 mM each) were added (on ice) and the mixture incubated at 37° C. for 2 min. Then, 1 µl reverse transcriptase (200 U/µl) solution was added and allowed to react at 37° C. for 1.5 hrs. The enzyme was inactivated by heating the mixture to 70° C. for 15 min. In some cases (to ensure single strandedness), cDNA's were treated with RNAse H (1.5 U/µl, PROMEGA). cDNA's were stored at −20° C.

RT-PCR of hCG-R and β2 Microglobulin

To aliquots of 1–6 µl (representing 20 ng cDNA) were added 2.5 µl primer solutions (100 ng/µl), 1 µl dNTP (10 mM each), 5 µl 10× PCR buffer supplemented with 1.5 mM $MgCl_2$ and 0.5 µl Taq polymerase (2 U/µl, DyNAZyme™ II, FINNZYMES Oy, Espoo, Finland). The mixture was incubated 2 min at 94° C., and then in 35 cycles 50 sec at 94° C., 1 min at 53° C. and 25 sec at 73° C. for hCG-R PCR using a thermocyler from Biometra (Gottingen, Germany). For β2 microglobulin-PCR annealing temperature was 56° C. and only 23 cycles were done. For hCG-R PCR the following primer pair was used:

5'-CCTGGAGGCCACGTTGACTTACCCCAG-3' (primer "hCG-R 5") (SEQ ID NO: 1)

5'-CCTAAGGAAGTCATAGCCCATAATG-3' (primer "hCG-R 6") (SEQ ID NO: 2)

The former matches a portion of exon 9 and the latter one portion of exon 11, thus covering a stretch of 285 bp of the hCG-R cDNA. The primer were obtained from MWG-Biotech (Ebersberg, Germany). For PCR of β2 microglobulin, the following primer pair was used:

5'-ATGCCTGCCGTGTGAACCATGT-3' (primer β2 micro sense) (SEQ ID NO: 3)

5'-AGAGCTACCTGTGGAGGAACCT-3' (primer β2 micro antisense) (SEQ ID NO: 4).

These primers match a portion of exon 2 and 4 respectively.

Aliquots of 10 µl of each of the PCR products were analysed by 1.5% agarose gel electrophoresis using ethidium bromide straining.

mRNA expression of the LH/hCG receptor was not evidenced in any of the four KS cell lines, whereas human testis, used as a control, clearly expressed the LH/hCG-R mRNA.

TABLE 1

| CELL LINE | CULTURE MEDIUM | PASSAGE NUMBER | CELL NUMBER IN CULTURE | mRNA YIELD (#) |
|---|---|---|---|---|
| M7/3 | A | 9 | 6X10E6 | — |
| | | | 1X10E7 | 0.89 |
| | | | 4X10E6 | — |
| | | | 4X10E6 | — |
| | | | 4X10E6 | 1.90 |

TABLE 1-continued

| CELL LINE | CULTURE MEDIUM | PASSAGE NUMBER | CELL NUMBER IN CULTURE | mRNA YIELD (#) |
|---|---|---|---|---|
| M5/1 | A | 7 | 2X10E6 | — |
|  |  | 10 | 2X10E6 | — |
|  |  | 11 | 3X10E6 | — |
|  |  | 13 | 1X10E6 | 1.40 |
| M7KK2 | A | 6 | 7X10E6 | 0.96 |
|  |  | 8 | 8X10E6 | — |
|  |  | 9 | 2X10E6 | 1.28 |
|  |  | 11 | 5X10E6 | — |
|  |  | 12 | 5X10E6 | 1.60 |
| KS10 | B | 15 | 1X10E7 | 0.96 |
|  |  | 18 | 8X10E6 | — |
|  |  | 20 | 2X10E7 | 5.60 |

Medium A: DMEM (Gibco), supplemented with 10% of FCS (Gibco), Penicillin (100 IU/ml) and Streptomycin (10 µg/ml).

Medium B: 50% of RPMI 1640+50% DMEM (Gibco), supplemented with 10% FCS (Gibco), Penicillin (100 IU/ml), Streptomycin (10 µg/ml), Glutamine (40 mM).

REFERENCES TO TABLE 1

M7/3; M5/1; M7KK2: These KS cell lines from different patients were all prepared according to M Stürzl et al., Oncogene 10: 2007–2016, 1995. KS10: R. Benelli et al., Cancer Letters, 100: 125–132, 1996.

EXAMPLE 2

Inhibition of Kaposi's sarcoma cell lines by impure hCG as opposed to non-inhibition by purified recombinant hCG Materials and Methods Cell Culture Cell lines of the previous example and additional cell line KS 11 (F. Bussolino et al., J. Clin. Invest. 96: 940–952, 1995) were grown under the tissue culture conditions described in Table 1, however without streptomycin and penicillin.

hCG preparations

Urinary hCG: 10,000 IU/ampoule; CG-10; Sigma Chemical, St. Louis, Mo.; Recombinant hCG: prepared according to J. Lustbader et al., J. Biol. Chem., 29: 14204–14212, 1987.

Cell Proliferation/Viability Assay

In order to monitor cell proliferation/viability, the following procedure was used, which is based on Boehringer Mannheim WST-1 reagent (Cat#1644, 807). This procedure colorimetrically measures the generation of a formazan salt in viable cells upon addition of the tetrazolium salt WST-1 (4-[3-(4-iodophenyl)-2-(4-nitrophenyl)-2H-5-tetrazolio]-1,3-benzene disulfonate). Dehydrogenases (i.e. the "succinate-tetrazolium reductase system", E. C. 1:3.99.1, a member of the respiratory chain enzyme system) present in mitochondria of viable cells cleave WST-1 to its dark red formazan derivative.

This derivative is chemically quite stable and water-soluble and thus can be directly measured in the culture medium. An augmentation in "WST-1" activity correlates with an increase in the number of viable and thus metabolically active cells.

The assay is very sensitive and can be performed with $1-2\times10^4$ cells per well, thus in a 96 well microtiter plate.

Results

Influence of hCG preparations on KS cells in culture

Cells were cultivated under standard conditions, as described earlier, distributed onto 96 well plates ($1-2\times10^4$ cells per well) and grown for 24 hours. The experiments described below refer to passage numbers 22–25 for KS11 cells, and passage #8–10 for M7kk2 cells. Thereafter, medium was changed for one containing only 0.5% FCS instead of 10%. After another 1–2 hours cultivation, drugs were added and cells incubated for 24 hours. Finally, WST-1 was added and 4 hours later, the formation of its red derivative was monitored at 450 nm in a microtiter well reader. All experiments were performed in quadruplicate. Readings were evaluated by Student's T tests.

CG10, a urinary hCG preparation made by Sigma inhibited cell viability (at a dose of 800 nM onwards, 1600 nM being the preferred dosage). Light microscopy examination, performed by means of an inverted mircoscope, showed that all cells were rounded or dead or fragmented into debris, in this order, depending on the time elapsed after addition of drug. Recombinant hCG, however, when tested under the same conditions, was not inhibitory, nor did it show cell proliferation enhancing effect.

EXAMPLE 3

Inhibition of Kaposi's sarcoma cell lines by Beta-core

Materials and Methods

Human Umbilical Vein Endothelial Cells (HUVEC) were obtained from ATCC (Rockville, Md., USA) and grown on gelatine pre-coated flasks (Sigma, 1% in distilled water) in M199 media supplemented with 10% heat inactivated (hi) FCS, Heparin (ICN, 100 µg/ml) and Endothelial Cell Growth Supplement (60 µg/mg). Urinary hCG (6,000 IU/mg) was prepared from crude urinary hCG as described in Lunardi-Iskandar, (1995). hCG β subunit according to the same method starting from r-hCG. hCG Beta-core was prepared according to Birken, 1988, with a further purification step by RP-HPLC.

Establishment of primary KS-cell cultures

KS biopsies were immediately put in RPMI medium supplemented with amphotericin B (2.5 µg/ml), penicillin (100 U/ml), and streptomycin (50 µg/ml). The lesions were then minced in small pieces that were subsequently used to obtain explants. Remaining portions of the biopsies were enzymatically digested with trypsin (0.25%) for 15 minutes at 37° C., then with Collagenase type I (400 U/ml) and type II (1000 U/ml) (Seromed) in PBS (lacking Calcium and Magnesium) for 2 hours at 37° C., and again with 0.5% trypsin, 15 minutes at 37° C. to disaggregate the remaining cell clusters. The cells obtained from enzymatic digestion were centrifuged and plated in gelatine coated 25 cc. flasks. Cells were cultured using 50% RPMI 1640/50% DMEM medium with 10% hi FCS. The primary ("reactive") KS spindle cells were obtained from an epidemic (AIDS 1ST KS 20) and a iatrogenic (1ST KS 26) biopsies using enzymatic digestion.

The biopsies used for primary cultures were positive for HHV-8 Kaposi associated herpes virus. Cells were characterised and found similar to previously described spindle cells (F. Bussolino, 1995).

Establishment of the KS IMM cell line and its characterisation

One KS biopsy (from a iatrogenic patient different from KS 26) gave rise to two different cell populations; "reactive" spindle cells, using enzymatic digestion, and a population of smaller cells arising from an explant. These cells were isolated and expanded; they grew rapidly with a doubling time of 24 hours and showed no signs of senescence after numerous passages of in vitro culture. This apparently "immortal" KS cell line was termed KS IMM. The KS IMM cells were cultured in simple DMEM 10% hi FCS.

Metabolic growth assays:

Cells ($1\times10^3$/well for KS IMM, $2\times10^3$/well for KS spindle cells and HUVE cells) were plated into 96-well microtiter plates with 150 µl complete medium. After 24 hours hCG or its derivatives were added dissolved in 150 µl of complete medium. Urinary hCG, β-subunit and Beta-core were used at different concentrations (40 µg/ml, 10 µg/ml and 5 µg/ml respectively) in order to have approximately the same molar concentration, the treatment was repeated once every 48 hours (urinary hCG) or every 24 hours (β-subunit and Beta-core). At the end of the treatment cells were incubated at 37° C. for 4 hours with MTT [3-(4,5-dimethylthiazol-2-yl)-2,5-diphenyl-tetrazolium bromide (thiazolyl blue)] by adding 50 µl of a 2 mg/ml solution (in PBS) to each well.

The plate was centrifuged for 10 minutes at 400× g and the solution with MTT removed. To elute the chromogen, 50 µl of DMSO at 37° C. were added, the plate was then incubated for 5 minutes at room temperature in the dark; absorbance (OD) was measured at 540 nm with a scanning multiwell spectrophotmer within 10 minutes after the addition of DMSO. To assess the specificity of the inhibitory activity of hCG and of its derivatives in the MTT assay we used specific neutralising antibodies (sheep anti hCG antibodies and rabbit anti β-subunit antibodies, Medix Biotech Inc.). Tests were performed using a compound/antibody molar ratio of 1:10.

Results

Effect of hCG and related derivatives on KS cell growth

The effects of urinary hCG, the β-subunit and the purified Beta-core on the growth of "reactive" KS spindle cells, KS IMM and HUVE cells were tested. KS spindle cells were partially growth inhibited by urinary hCG. The β-subunit of hCG gave an even greater inhibition. The most potent effect was obtained with the Beta-core fragment, which blocked growth of spindle cells and had no effect on growth of cultured normal human umbilical vein endothelial cells (HUVEC) used as a control (FIG. 1). The Beta-core was active on KS spindle cells also at 0.5 µg/ml concentration (not shown). Antiserum to hCG was able to counteract hCG inhibition of KS cell growth, whereas non-immune serum had no effect.

In a parallel experiment, KS IMM cell growth was inhibited by urinary hCG (20 µg/ml)with decrements in growth rate similar to the KS spindle cells. The β-subunit and Beta-core of hCG retained the inhibitory effect on KS IMM cell growth at an approximately 10 fold lower molar concentration showing more pronounced inhibition as compared to the intact hCG molecule. This was particularly evident for the Beta-core fragment, which showed the strongest inhibitory effect on KS IMM cells and the "reactive" KS spindle cells. The Beta-core was active at ten fold lower molar concentration than that reported by Lunardi-Iskandar for the β-subunit [Lunardi-Iskandar, 1995]. Growth of control HUVE endothelial cells was not inhibited.

In conclusion, all tested forms of hCG, were able to inhibit KS cells growth, the Beta-core being the most effective, also at lower doses. Growth rates obtained using MTT were confirmed by data obtained by direct cell counts with Trypan Blue.

---

What is claimed is:

1. A method for the treatment of Kaposi's sarcoma, comprising:

administering to a Kaposi's sarcoma patient an effective amount of a principle selected from the group consisting of hCG Beta-core, deglycosylated hCG, deglycosylated LH, and a mixture of two or more thereof.

2. A method in accordance with claim 1, wherein said principle is hCG Beta-core.

3. A method in accordance with claim 1, wherein said principle is deglycosylated hCG.

4. A method in accordance with claim 1, wherein said principle is deglycosylated LH.

5. A method in accordance with claim 1, wherein said principle is a mixture of two or more of hCG Beta-core, deglycosylated hCG and deglycosylated LH.

* * * * *